United States Patent [19]

Amishima

[11] Patent Number: 4,798,194
[45] Date of Patent: Jan. 17, 1989

[54] MAGNETIC THERAPEUTIC DEVICE

[75] Inventor: Shigeaki Amishima, Himeji, Japan

[73] Assignee: Aso Pharmaceutical Co., Ltd., Kikuchi, Japan

[21] Appl. No.: 953,523

[22] Filed: May 19, 1987

Related U.S. Application Data

[63] Continuation of Ser. No. 779,729, Sep. 24, 1985, abandoned.

[30] Foreign Application Priority Data

Nov. 12, 1984 [JP] Japan ............................. 59-171834[U]

[51] Int. Cl.⁴ ................................................ A61N 1/42
[52] U.S. Cl. .......................................... 128/9; 335/302; 128/15
[58] Field of Search ...................... 128/1.3, 1.5; 335/302–305

[56] References Cited

U.S. PATENT DOCUMENTS

| | | | |
|---|---|---|---|
| 3,784,945 | 1/1974 | Baermann | 335/302 |
| 3,921,620 | 11/1975 | Nakayama | 128/1.3 |
| 4,162,672 | 7/1979 | Yazaki | 128/1.3 |
| 4,391,270 | 7/1983 | Uragami | 128/1.3 |
| 4,480,596 | 11/1984 | Shumiyashu | 128/1.3 |
| 4,489,711 | 12/1984 | Latzke | 128/1.3 |

FOREIGN PATENT DOCUMENTS

| | | | |
|---|---|---|---|
| 646314 | 11/1928 | France | 128/1.5 |
| 2371916 | 7/1978 | France | 128/1.3 |
| 81/00357 | 2/1981 | PCT Int'l Appl. | 128/1.3 |
| 84/00305 | 2/1984 | PCT Int'l Appl. | 128/1.3 |

OTHER PUBLICATIONS

Mansfield et al., NMR Imaging in Biomedicine, Academic Press, 1982, N.Y., pp. 297–310.

Primary Examiner—Francis J. Jaworski
Assistant Examiner—John C. Hanley
Attorney, Agent, or Firm—Jordan and Hamburg

[57] ABSTRACT

This invention provides a sticking type magnetic therapeutic device having both N- and S-poles formed on one side of a permanent magnet body, whereby emitted magnetic lines of force are totally applied within the human body, resulting in effectual and effective application during therapeutic treatment, while avoiding the ill effect of extraneous magnetic lines of force on other electronic items such as magnetic cards, wrist watches or the like.

11 Claims, 3 Drawing Sheets

MAGNETIC THERAPEUTIC DEVICE

This application is a continuation of application Ser. No. 779,729, filed Sept. 24, 1985, now abandoned.

BACKGROUND OF THE INVENTION

The present invention relates to the improvement of a magnetic therapeutic device for curing the stiffness of the body or the like by means of penetration of magnetic lines of force in sticking a permanent magnet body on the human skin.

Conventionally, this kind of magnetic therapeutic device offers sticky plaster sheet mounted with a permanent magnet of a disk-like shape or a permanent magnet having a small projection on its surface.

In either case, however, as shown in FIG. 10, the N-pole 21 being mounted on the side contacting the skin and the S-pole 22 on the reverse side, the magnetic lines of force are emitted from the N-pole 21 and return to the S-pole 22, forming loops (shown in broken line in the illustration) when the permanent magnet is 23 is stuck on the skin surface 11. For this reason the return magnetic lines of force are wasted outside the human body, not effectively contributing therapeutically. Besides, such externally working magnetic field will exhibit an ill effect on various electronic devices such as a magnetic card or a wrist watch.

SUMMARY OF THE INVENTION

The magnetic therapeutic device according to the present invention is provided with a sticking plaster sheet having a sticky surface on one side of it and a permanent magnet body of an oval shape in plan view attached onto the sticking surface of the sheet. The above-mentioned permanent magnet body has a magnetized portion having both magnetic poles of the N- and the S-pole arranged on the opposite surface of the magnet to the sticking sheet and a non-magnetized portion arranged on the same side surface of the magnet to the sticking sheet.

It is an object of the present invention, therefore, to provide a magnetic therapeutic device which eliminates the loss of magnetic lines of force outside of the human body and uses them most efficiently, avoiding any ill effect on a magnetic card and the like.

The above object, features and effect of the present invention will become more apparent from the following detailed description referring to the accompanying drawings.

DETAILED DESCRIPTION OF THE PREFERRED EMBODIMENTS

Figure 1:
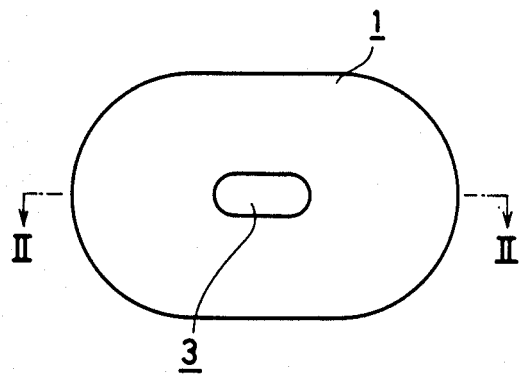
FIG. 1 is a plan view of a magnetic therapeutic device according to the invention.
Figure 2:
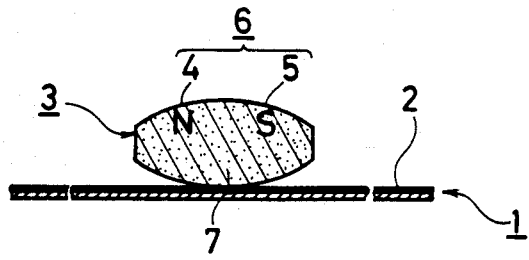
FIG. 2 is a sectional view along the line II—II of FIG. 1.

FIGS. 1 and 2 show the magnetic therapeutic device according to the invention. A permanent magnet body of ferrite 3 is mounted onto a sticking surface 2 of a sticking sheet 1. The example shown has the sticking sheet 1 and the permanent magnet body 3, both of oval shap in plan form. The sticking sheet 1 is not limited in form, however, to the example shown above and can take optional forms of different shapes. Furthermore, the permanent magnet body 3 is formed into a shape having about 5–7 mm in longitudinal dimension and about 3–5 mm in a shorter longitudinal dimension, and into a convex shape thicker in the center and thinner in the periphery.

This invention is characterized in the form and the arrangement of magnetic poles of said permanent magnet body 3 in that a magnetized portion 6 having both magnetic poles 4 and 5 of the N- and the S- pole on the opposite side surface of the magnet to the sticking sheet 1 is formed, while a non-magnetized portion 7 on the same side surface of the magnet to the sticking sheet is also formed.

The above-mentioned N-pole 4 and the S-pole 5 are disposed at the end portions of the longitudinal side of the permanent magnet body 3, which is due to the reasons given below:

(1) Since an area not magnetized is naturally developed between the N-pole 4 and the S-pole 5, each area of the N- and S-pole can be made large, accordingly increasing the strength of the magnetic field, by taking an oval shape for the magnet body and the arrangement of the poles along the longitudinal side.

(2) By taking a proper width for the non-magnetized area above-mentioned and making the distance between the N-pole 4 and the S-pole 5 fairly long, the loop of the magnetic field can be made sufficiently large and deep in reach.

Figure 3:
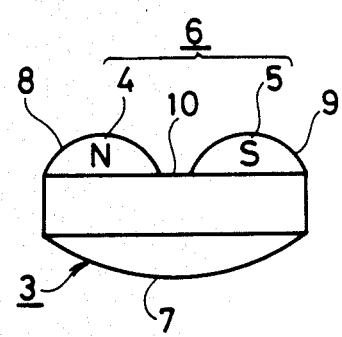
FIG. 3 is an elevation view of a permanent magnet body of another embodiment.
Figure 4:
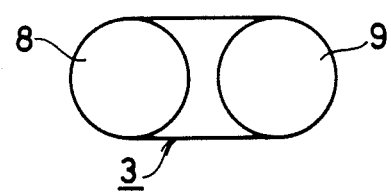
FIG. 4 is a plan view of the embodiment of FIG. 3.

FIGS. 3 and 4 show another embodiment of the permanent magnet body 3, in which two hemispheric projections 8 and 9 are arranged on the side of the magnetized portion 6 of the permanent magnet body 3 in one body with the rest of the magnet, and the N-pole 4 and the S-pole 5 correspond to the projections 8 and 9 respectively.

According to this embodiment, each projection 8 or 9 gives a stimulus by strong press on a skin surface, thereby the finger-pressure effect is expected.

Figure 5:
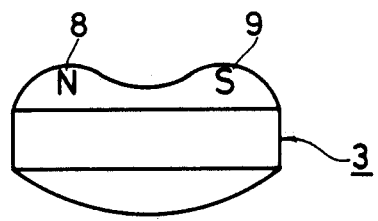
FIG. 5 is an elevation view of a permanent magnet body of still another embodiment.

FIG. 5 shows a modification of the embodiment in FIGS. 3 and 4 in which a slot portion 10 between the projections 8 and 9 is filled up to form a continuously gently-sloping curved surface. According to this embodiment, it provides advantages that permit easy formation of the permanent magnet body 3 as compared with the embodiment in FIGS. 3 and 4, together with obtaining an appropriate stimulus by pressing the projections 8 and 9.

Figure 6:
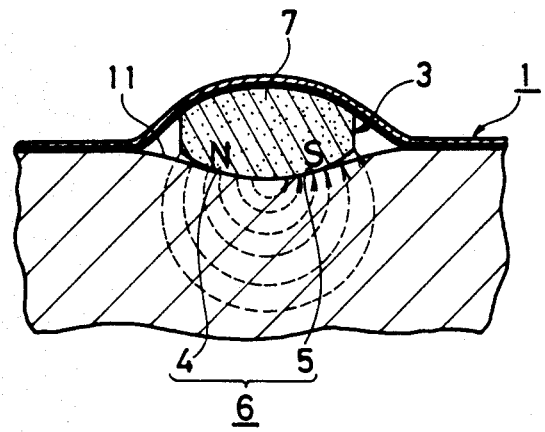
FIGS. 6 and 7 are section views showing sticking states of the magnetic therapeutic devices and distributions of the magnetic lines of force.

When the magnetic therapeutic device of the first embodiment in FIGS. 1 and 2 is applied to the skin surface 11, almost the entire surface of the magnetized portion 6 contacts the skin surface 11 as illustrated in FIG. 6, and the magnetic lines of force emitted from the N-pole 4 (as shown in broken lines) penetrate into and operate on the human body, and thereafter reach the S-pole 5. Consequently, the magnetic lines of force do not operate outside the human body and do not form an external magnetic field.

Figure 7:
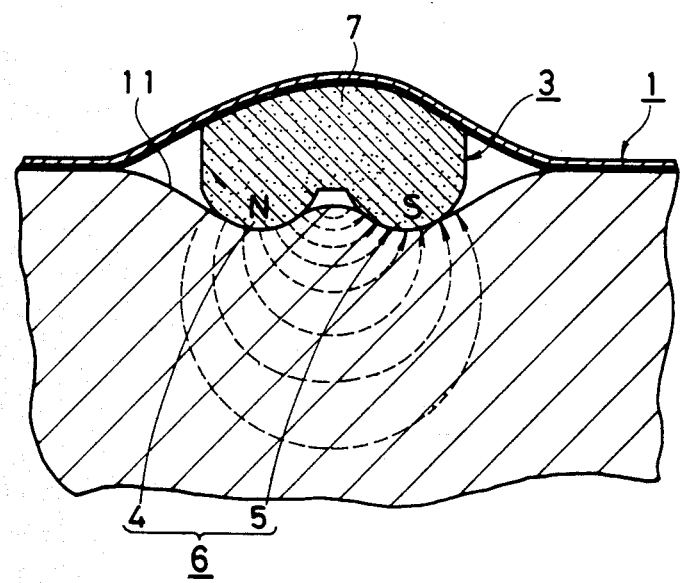

FIG. 7 illustrates the state in which the magnetic therapeutic device of the second embodiment in FIGS. 3 and 4 is applied to the skin surface 11, and in this case, the magnetic lines of force operate only within the human body and do not operate outside the human body.

Figure 8:
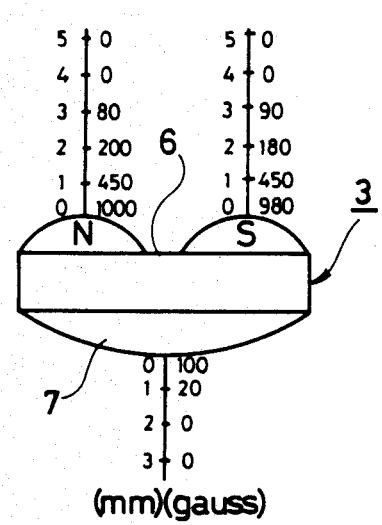
FIGS. 8 and 9 are explanatory drawings showing comparisons of measurements of the magnetic field strengths.
Figure 9:
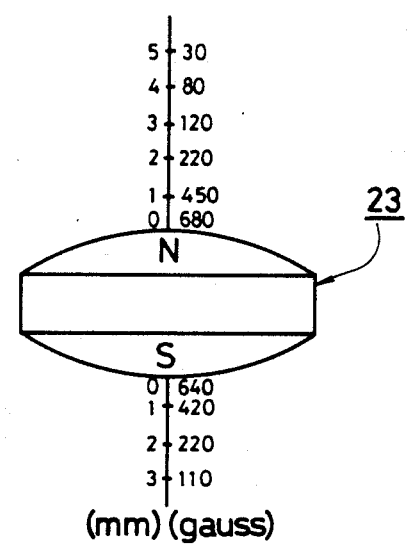
Figure 10:
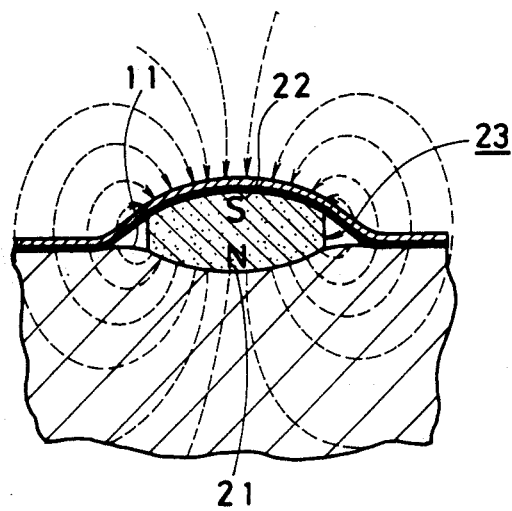
FIG. 10 is a section view showing a sticking state and a distribution of the magnetic field strengths of a conventional type of device.

FIGS. 8 and 9 show measurements of magnetic field strength (gauss) on both sides of the magnetic VS distances (mm) which are taken, by the gaussmeter, for the permanent magnet body 3 having one side magnetized portion according to the invention and the permanent magnet body 23 having both side magnetized portions of a conventional type. Referring to the same figures, it is understood that for the permanent magnet body 3 according to the invention, the magnetic field strength outside the non-magnetized portion 7 is so low that the effect of the magnetic lines of force may be neglected on the side of the non-magnetized portion 7.

In the summary of the invention, both magnetic poles of an N- and an S-pole are formed on the opposite surface of a permanent magnetic body to a sticking sheet in the magnetic therapeutic device in which the permanent magnet body is attached to a sticking surface of the sticking sheet as mentioned above. The form of the magnetic body is made oval shape in plan view, and so magnetic lines of force emitted from the N-pole of the permanent magnet body penetrate into the human body and thereafter read the S-pole when the device is applied to a skin surface. Therefore, the magnetic lines of force do not operate outside the human body. This prevents the magnetic lines of force from operating unselessly outside the human body and enables the device to use the magnetic lines of force most efficiently and allows the device to improve greatly the effect of magnetic therapy as compared with the body side-pole type of permanent magnetic body having the same volume and weight as the one side-pole type of permanent magnet body. Further, there is no magnetic field outside the human body and so the magnetic field and magnetic lines of force outside the human body do not have any adverse effect on electronic devices such as various kinds of magnetic cards and wrist watches and the like. As a result of attaining the objects of the invention, notable effects as mentioned above can be produced.

While preferred embodiments of the invention have been disclosed, many modifications and variations thereto are possible for those skilled in the art within the true spirit and scope of the invention. Accordingly, the scope of the invention is defined only by the attached claims.

What is claimed is:

1. A magnetic therapeutic device comprising a sheet having a sticking surface, a permanent magnetic body having a first side and a second side, said first side being opposite to said second side, said first side being mounted on said sticking surface of said sheet, said second side being adapted to contact a human body part, said magnetic body having a first portion and a second portion, said first portion being defined partially by said first side and said second portion being defined partially by said second side, said first and second portions being disposed on opposite sides of a bisecting plane disposed generally midway between said first and second sides, said first portion being non-magnetized, said second portion being magnetized and containing a north pole and a south pole in side-by-side relationship and facing said second side such that said second side is thereby magnetized and substantially all of the magnetic lines of force from said magnetized second side pass outwardly of said second side, whereby substantially all of the magnetic lines of force from said permanent magnetic body pass outwardly of said second side and penetrate into said human contacting part.

2. A magnetic therapeutic device according to claim 1, wherein the field strength at the surface of said magnetized second side is at least 980 gauss.

3. A magnetic therapeutic device according to claim 1, wherein the field strength at at least a portion of the surface of said magnetized second side is about 1000 gauss.

4. A magnetic therapeutic device according to claim 1, wherein the field strength at the surface of said magnetized second side is at least 9.8 times greater than the field strength at the surface of said first side.

5. A magnetic therapeutic device according to claim 1, wherein the field strength at 1 mm distance from the surface of said magnetized second side is at least 22.5 times greater than the field strength at 1 mm distance from the surface of said first side.

6. A magnetic therapeutic device according to claim 1, wherein the field strength at a 2 mm or greater distance from the surface of said first side is substantially zero.

7. A magnetic therapeutic device according to claim 6, wherein the field strength at a 2 mm distance from the surface of said magnetized second side is at least 180 gauss.

8. A magnetic therapeutic device according to claim 1, wherein the field strength of said second side ranges between 980 and 1000 gauss at 0 mm from said north and south poles respectively to 80 and 90 gauss at 3 mm from said poles.

9. A magnetic therapeutic device according to claim 1, wherein said permanent magnetic body has a generally convex shape with a thicker center and relatively thinner periphery.

10. A magnetic therapeutic device according to claim 1, wherein said second side has first and second hemispheric projections for contacting said human body part and said north and south poles are contained, respectively, in said first and second hemispheric projections.

11. A magnetic device adapted to be worn by a person and useable in the presence of and juxtaposed to magnetic-sensitive devices without having any ill effects on said magnetic-sensitive devices, comprising a sheet having a sticking surface, a permanent magnetic body having a first side and a second side, said first side being opposite to said second side, said first side being mounted on said sticking surface of said sheet, said second side being adapted to contact a human body part, said magnetic body having a first portion and a second portion, said first portion being defined partially by said first side and said second portion being defined partially by said second side, said first and second portions being disposed on opposite sides of a bisecting plane disposed generally midway between said first and second sides, said first portion being non-magnetized, said second portion being magnetized and containing a single north pole and a single south pole in side-by-side relationship and facing said second side such that said second side is thereby magnetized and substantially all of the magnetic lines of force from said magnetized second side pass outwardly of said second side while a substantially lesser amount of said lines of force pass from said first side, whereby substantially all of the magnetic lines of force from said permanent magnetized body pass outwardly of said second side and penetrate into said contacting human body part without having any ill effects on any juxtaposed magnetic-sensitive devices.

* * * * *

UNITED STATES PATENT OFFICE
CERTIFICATE OF CORRECTION

Patent No. 4,798,194      Dated January 17, 1989

Inventor(s) Shigeaki AMISHIMA

It is certified that error appears in the above-identified patent and that said Letters Patent is hereby corrected as shown below:

On the first page of the patent, change the Appl. No. from "953,523" to --053,523--.

Signed and Sealed this

Eighteenth Day of July, 1989

Attest:

DONALD J. QUIGG

Attesting Officer      Commissioner of Patents and Trademarks